(12) United States Patent
Dua et al.

(10) Patent No.: US 8,029,494 B2
(45) Date of Patent: Oct. 4, 2011

(54) METHOD OF REMOVING BILIARY STONES WITH COAXIAL CATHETER DEVICE

(75) Inventors: Kulwinder S. Dua, Brookfield, WI (US); Greg J. Skerven, Kernersville, NC (US); David M. Hardin, Jr., Winston-Salem, NC (US); Kenneth J. Fearn, Winston-Salem, NC (US); Pushkar S. Mukewar, Boston, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 701 days.

(21) Appl. No.: 11/585,513

(22) Filed: Oct. 24, 2006

(65) Prior Publication Data

US 2007/0197997 A1    Aug. 23, 2007

Related U.S. Application Data

(60) Provisional application No. 60/730,236, filed on Oct. 24, 2005.

(51) Int. Cl.
*A61M 31/00* (2006.01)

(52) U.S. Cl. ...................................... 604/509

(58) Field of Classification Search ............. 604/102.01, 604/915–917, 920–921, 508–510, 96.01, 604/103.02
See application file for complete search history.

(56) References Cited

U.S. PATENT DOCUMENTS

| | | | |
|---|---|---|---|
| 4,627,837 A | 12/1986 | Gonzalo | |
| 5,334,143 A * | 8/1994 | Carroll | 604/514 |
| 5,547,469 A | 8/1996 | Rowland et al. | |
| 5,599,299 A | 2/1997 | Weaver et al. | |
| 5,788,681 A | 8/1998 | Weaver et al. | |
| 5,792,094 A * | 8/1998 | Stevens et al. | 604/4.01 |
| 5,843,028 A | 12/1998 | Weaver et al. | |
| 5,868,698 A | 2/1999 | Rowland et al. | |
| 6,190,357 B1 * | 2/2001 | Ferrari et al. | 604/102.01 |
| 6,508,784 B1 * | 1/2003 | Shu | 604/96.01 |
| 6,692,484 B1 * | 2/2004 | Karpiel et al. | 604/544 |
| 6,770,066 B1 | 8/2004 | Weaver et al. | |
| 2002/0151870 A1 * | 10/2002 | Grimes et al. | 604/509 |
| 2003/0130679 A1 | 7/2003 | Aliperti et al. | |
| 2005/0143770 A1 * | 6/2005 | Carter et al. | 606/170 |
| 2006/0149218 A1 * | 7/2006 | Slater et al. | 604/509 |
| 2006/0195117 A1 | 8/2006 | Rucker et al. | |

* cited by examiner

*Primary Examiner* — Nicholas D Lucchesi
*Assistant Examiner* — Weng Lee
(74) *Attorney, Agent, or Firm* — Brinks Hofer Gilson & Lione

(57) ABSTRACT

A method of removing an obstruction in the biliary duct including the steps of providing a coaxial catheter device comprising an inner catheter having a proximal end and a distal end wherein at least two or more lumens are formed between the proximal end and distal end of the inner catheter. The method includes providing an outer catheter having a proximal end and a distal end and an opening wherein the inner catheter is coaxially engaged through the opening of the outer catheter thereby forming a coaxial space between the inner catheter and the outer catheter wherein at least one of the two or more lumens is configured for receiving a fluid for inflating a balloon, at least one of the first lumen and the second lumen is configured for receiving a wire guide and the coaxial space is configured for receiving a flushing fluid for the removal of an obstruction within the biliary duct.

20 Claims, 7 Drawing Sheets

METHOD OF REMOVING BILIARY STONES WITH COAXIAL CATHETER DEVICE

RELATED APPLICATIONS

This application claims priority to provisional application No. 60/730,236 filed on Oct. 24, 2005, the entire disclosure of which is incorporated by reference herein.

FIELD OF THE INVENTION

The present invention relates to the field of medical devices, and more particularly to medical devices for advancement through passageways of the body during medical procedures.

BACKGROUND

Catheters are used during many medical procedures in the gastrointestinal system, including the pancreatobiliary system (i.e., the biliary tree), the stomach, and the esophagus. During vascular procedures, such as balloon angioplasty, stent placement, and endoluminal grafts for aortic aneurysms, the use of catheters are essential in evaluating the site of the particular obstruction in the affected artery. For example, catheters are inserted into canals, vessels, and passageways of the body to permit injection or withdrawal of fluids, or to keep the passageway open. Catheters also provide access to a passageway of the patient while a physician performs various procedures. For example, catheters are often utilized to perform varying medical procedures, such as the deployment of stents and biopsy procedures.

Catheters are also inserted through endoscopes during the diagnosis and treatment of several medical conditions. One such medical procedure utilizing a catheter device is Endoscopic Retrograde Cholangiopancreatography (ERCP). During ERCP procedures the catheter tends to experience many difficulties due to the various functions of the particular catheter. For example, during procedures involving identifying obstructions within the biliary or pancreatic duct, a catheter may be utilized to insert a wire guide and advance other medical devices over the wire guide. Additionally, the catheter may be utilized to pass contrast medium to identify obstructions such as bile duct stones. The catheter may also be utilized for flushing or passing fluids. Regardless of the medical procedure performed, the catheter can experience problems associated with friction or the leakage of bodily fluids due to the constant removal and insertion of medical devices through the catheter or the use of multiple catheters.

Due to the complexity of the particular medical procedure, physicians often need to insert additional medical devices through the catheter (or the endoscope) during the medical procedure. Thus, many medical procedures often require the use of two or more catheters and catheter exchanges. However, due to the difficulty associated with catheter exchanges and the time associated with the insertion and removal of medical devices into the catheter, the task of positioning and maneuvering medical devices through the catheter or the positioning of multiple catheters can become difficult and time consuming. Additionally, catheter exchanges tend to shift the focus of the assistant from other areas of responsibility, such as checking the patient, checking monitors for relevant information, or carrying out other tasks.

As a way of simplifying procedures involving catheters, devices have been developed that include multiple lumen combinations. One device includes a multiple lumen catheter that requires a first, a second, and a third lumen wherein each lumen functions respectively to inject a contrast agent, perform a sphincterotomy and dislodge gallstones. The lumens of the catheter extend parallel to each other between a proximal and distal end of the device. A problem with this type of device is that the lumen sizes of the catheter are restricted and the functionality of the device is limited to particular medical procedures. As a result of the size limitations of the lumens of the catheter, it is difficult to pass flushing fluids within the lumens of the catheter. Specifically, the space between the lumens of the catheter is not large enough to create the necessary hydraulic force for properly removing gallstones or similar objects. Therefore, the lumens of the catheter may become clogged during use thereby preventing the removal of gallstones or similar dislodged objects with the device.

Another catheter device available in the prior art includes the use of balloons in the removal of common bile duct stones. This type of device includes a catheter balloon that is passed beyond the stones and then positioned adjacent to the upstream side of the stones. Once positioned, the catheter balloon is inflated and the entire assembly is withdrawn outwardly until the stone has been pulled out through an incision in the common duct. The catheter utilizes the balloon for the purpose of removing stones from the common bile duct by retrograde movement of the stone through the incision in the common duct. However, use of this type of catheter device can become time consuming and inconvenient because of the time associated with performing the medical procedure using this complex assembly, and the increased risk resulting from removing stones through an incision.

What is needed is a catheter device that allows medical devices to be quickly and easily inserted into the gastrointestinal system for flushing the biliary duct of a patient, reduces the need for multiple catheter exchanges, and requires minimal time for a physician to operate and perform functions during the removal of obstructions within the biliary duct of a patient.

SUMMARY

The invention relates to medical devices for advancement through passageways of the body during medical procedures. More specifically, one aspect of the invention relates to a method of removing an obstruction in the biliary duct comprising the step of providing a coaxial catheter device comprising an inner lumen catheter having a proximal end and a distal end wherein two or more lumens are formed between the proximal end and the distal end of the inner lumen catheter. The method further comprises the step of providing an outer catheter having a proximal end and a distal end and an opening wherein the inner lumen catheter is coaxially engaged through the opening of the outer catheter thereby forming a coaxial space between the inner lumen catheter and the outer catheter. At least one of the two or more lumens of the coaxial catheter device is configured for receiving a fluid for inflating a balloon. In addition, at least one of the two or more lumens of the coaxial catheter device is configured for receiving a wire guide. The coaxial space of the coaxial catheter device is configured for receiving a fluid for the removal of an obstruction within the biliary duct. Additionally, the outer catheter may include a sheath or similar device providing a secondary lumen.

In another aspect of the present invention, the method of removing an obstruction in the biliary duct can comprise the step of providing a coaxial catheter device comprising a side port extending from the proximal end to the distal end of the inner catheter wherein the side port is utilized to transport fluid such as water, contrast and saline. The side port may operate in conjunction with the coaxial space to produce a hydraulic force to remove stones from the biliary duct.

In yet another aspect of the present invention, the method of removing an obstruction in the biliary duct can comprise the step of providing a coaxial catheter device comprising an exit port located along a portion of the coaxial catheter device. The coaxial catheter device can also include an inflation balloon engaged to the distal end of the catheter device.

In another aspect of the present invention, the method of removing an obstruction in the biliary duct can comprise the step of providing a coaxial catheter device comprising a connector having a first port engaged to a first conduit, a second port engaged to a second conduit and a third port engaged to a third conduit. The first conduit communicates with a first lumen having a first diameter, the second conduit communicates with a second lumen having a second diameter and the third conduit communicates with a coaxial space having a third diameter. The third diameter is larger than both the first diameter and the second diameter for providing an increased hydraulic force for the removal of an obstruction in the biliary duct. One skilled in the art will understand that a variety of lengths and diameters can be used within the design of the coaxial catheter device and fall within the scope of the invention. The coaxial catheter device may further comprise a radiopaque marker engaged along a surface of the coaxial catheter device. In addition, the coaxial catheter device may comprise a coating applied to at least a portion of the coaxial catheter device.

In yet another aspect of the present invention, a method of treating a subject comprises the step of implanting a coaxial catheter device at a point of treatment, the coaxial catheter device comprising an inner catheter providing at least two or more lumens coaxially engaged through an outer catheter forming a coaxial space between the inner catheter and the outer catheter. At least one of the two or more lumens is configured to receive a fluid for inflating a balloon. In addition, at least one of the two or more lumens is configured to receive a wire guide. The coaxial space is configured to receive a fluid for removing obstructions from the biliary duct.

The invention includes other embodiments within the scope of the claims, and variations of all embodiments, and is limited only by the claims made by the Applicants. Additional understanding of the invention can be obtained by referencing the detailed description of embodiments of the invention below, and the appended drawings.

DESCRIPTION OF THE INVENTION

Figure 1:
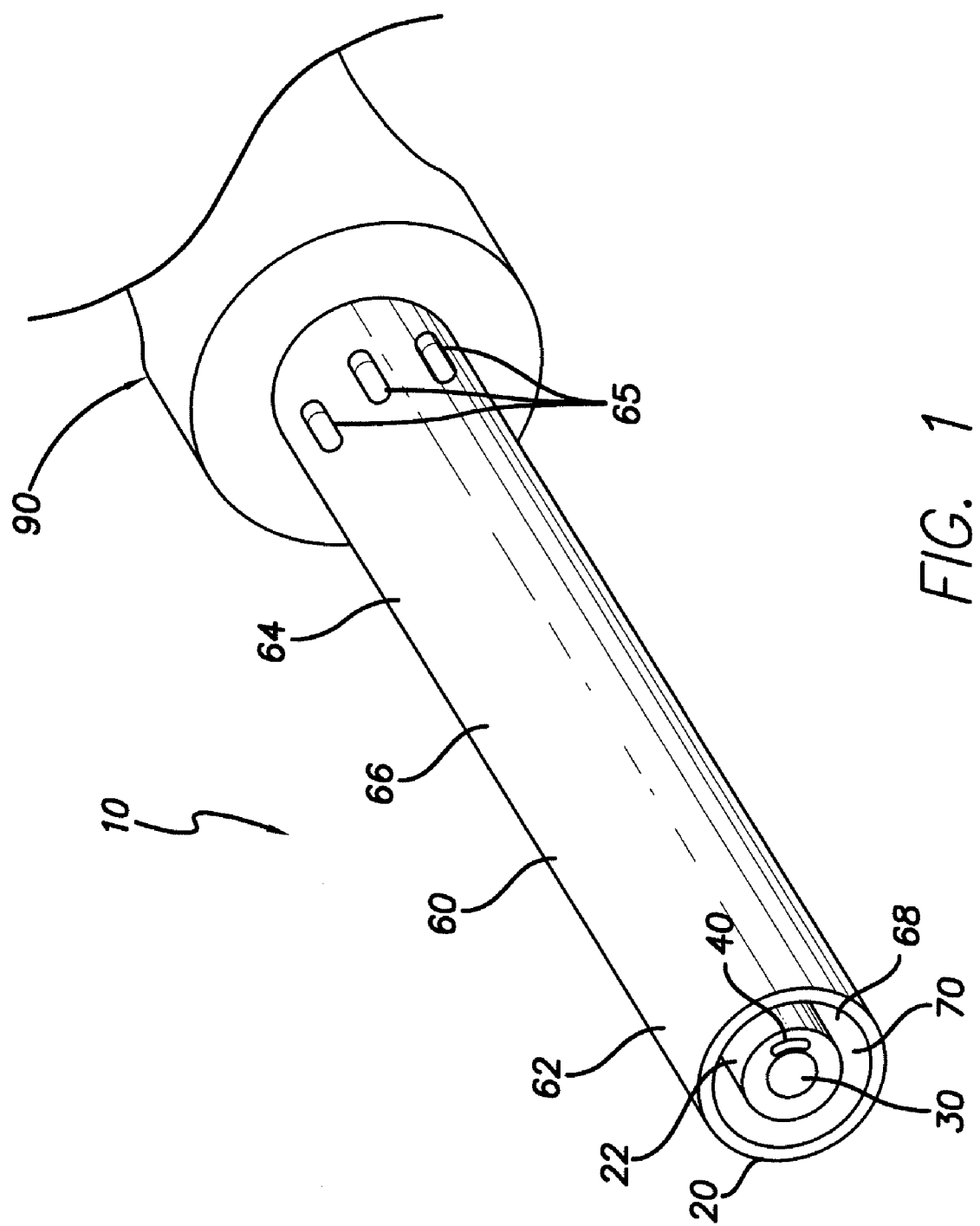
FIG. 1 shows a perspective view of a coaxial catheter device of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale and in certain instances details have been omitted, which are not necessary for an understanding of the present invention, such as conventional fabrication and assembly.

Referring now to FIG. 1, a first embodiment of a coaxial catheter device 10 of the present invention is shown. The coaxial catheter device 10 includes an inner catheter 20 coaxially placed inside an outer catheter 60. The inner catheter includes a proximal end 22, a distal end 24 and a tubular body 26 (see FIG. 2). The inner catheter 20 further includes a first lumen 30, a second lumen 40 and a side port 50 extending between the proximal end 22 and the distal end 24 of the inner catheter 20 (see FIG. 2). The outer catheter 60 includes a proximal end 62, a distal end 64 and a tubular body 66. The outer catheter 60 further provides a lumen or opening 68 extending between the proximal end 62 and distal end 64 of the outer catheter 60. The inner catheter 20 is inserted into the opening 68 and extends along at least a portion of the length of the outer catheter 60 thereby forming a coaxial space 70. The coaxial space 70 is comprised of the portion of the opening 68 between the inner catheter 20 and the outer catheter 60. Additionally, the outer catheter 60 may include a sheath or similar device providing a secondary lumen.

Figure 2:
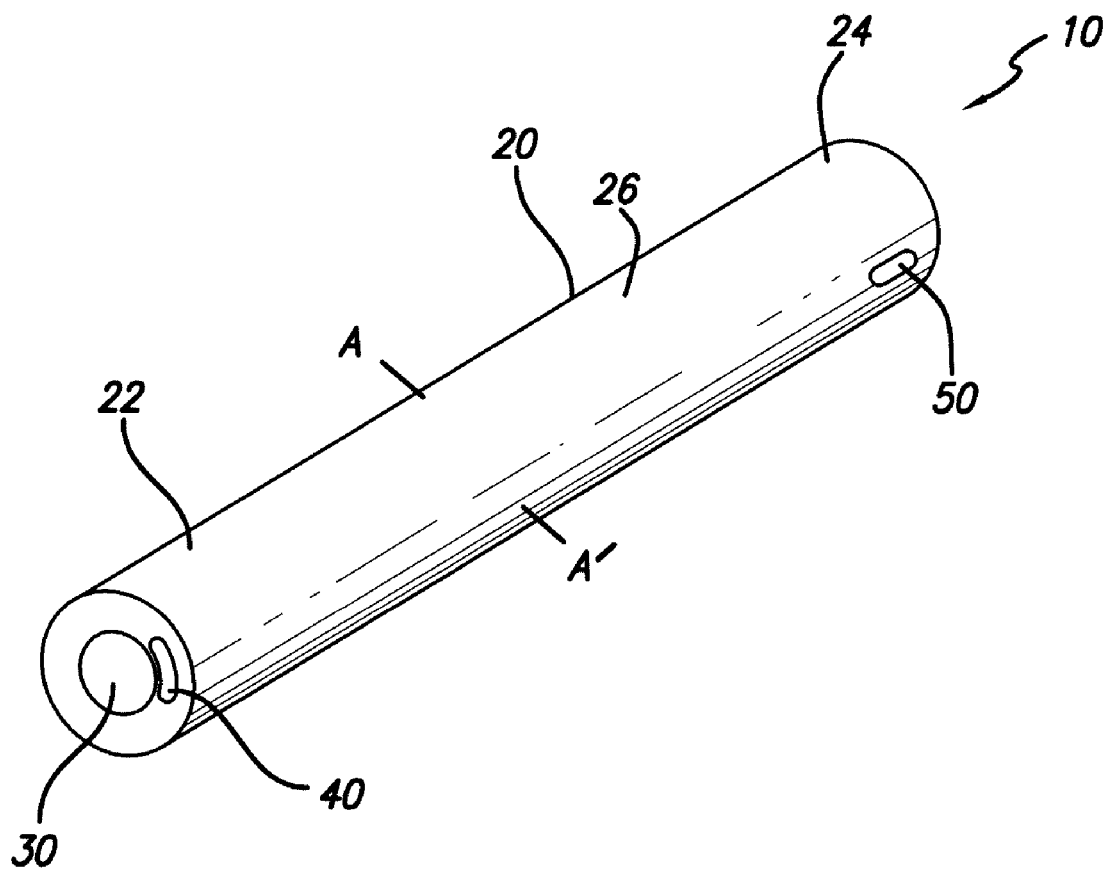
FIG. 2 shows a perspective view of a dual lumen catheter of the present invention.

In the embodiment illustrated in FIG. 1, the coaxial catheter device 10 is elongate and has a cylindrical shape. The optimal length of the coaxial catheter device 10 is determined by considering factors such as design and material used, as well by what is determined through experimentation to work best. In a preferred embodiment, the coaxial catheter device 10 has a length of 200 cm. As illustrated in FIG. 2, the inner catheter 20 is of sufficient length to pass through the opening 68 of the outer catheter 60, thereby forming the coaxial space 70. The length of the overall coaxial catheter device 10 is sufficient to allow a physician to perform a desired medical procedure, such as an ERCP procedure. Of course, one skilled in the art will understand that a variety of lengths and diameters of the inner catheter 20 and the outer catheter 60 of the coaxial catheter device 10 can be used.

Figure 3:
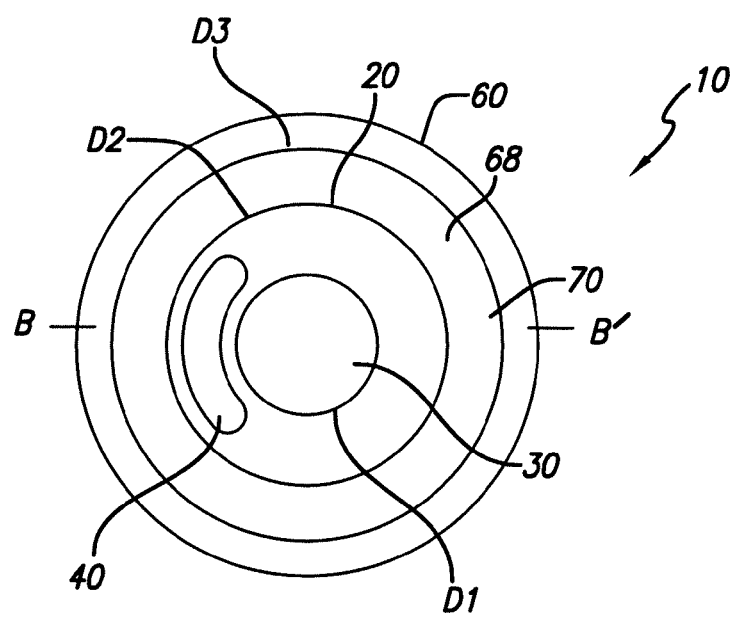
FIG. 3 shows a cross-sectional view taken along lines A-A' in FIG. 2.
Figure 4:
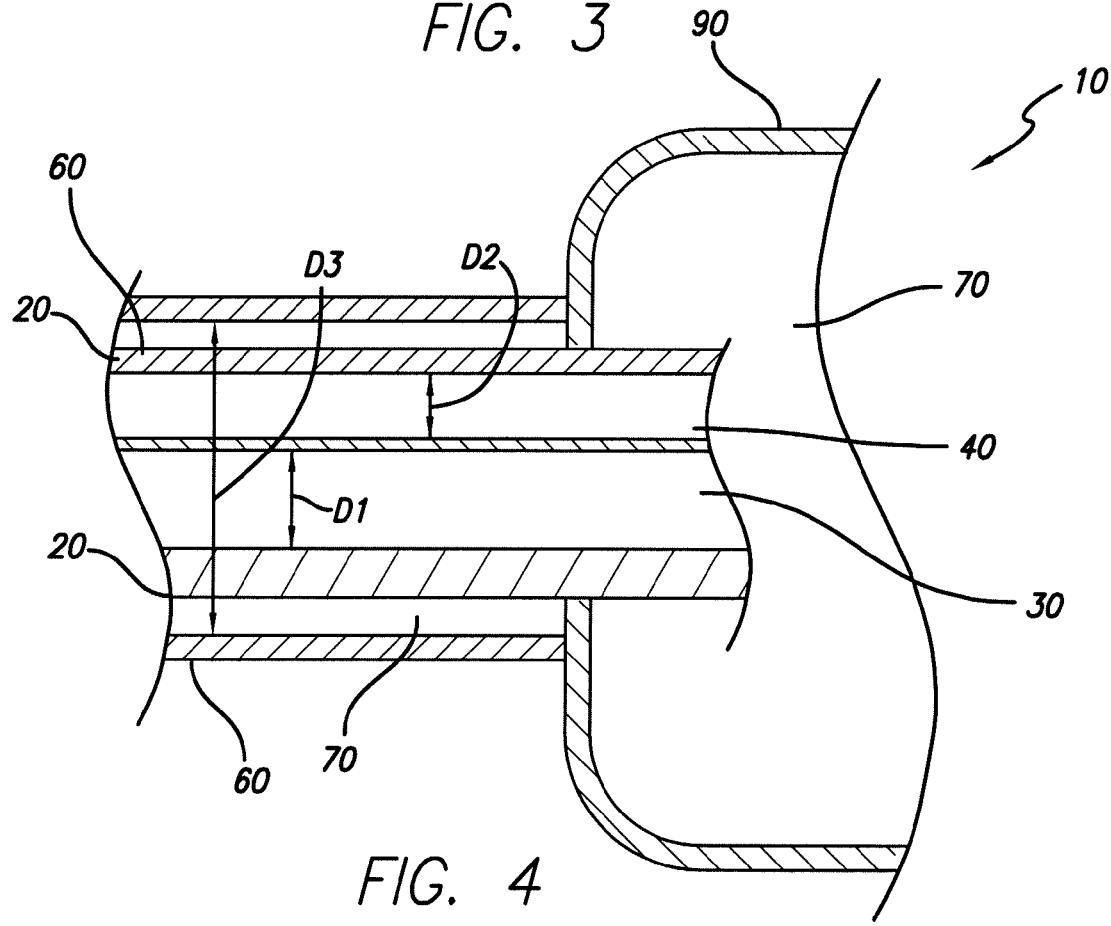
FIG. 4 shows a cross-sectional view taken along lines B-B' in FIG. 3.

Referring to FIGS. 3-4, the coaxial catheter device 10 comprises a plurality of lumens 30, 40 configured to receive a plurality of elongate medical devices. Specifically, at least one of the first lumen 30 and second lumen 40 of the coaxial catheter device 10 is adapted for use as an inflation lumen. In addition, at least one of the first lumen 30 and second lumen 40 of the coaxial catheter device 10 is adapted for use as a wire guide lumen. The coaxial space 70 of the coaxial catheter device 10 is adapted for use as a fluid lumen. The coaxial space 70 provides an increased diameter wherein fluids may be easily passed. Additionally, the design of the coaxial space 70 provides for an increase in hydraulic force to adequately flush stones from the bile duct into the duodenum.

In the embodiment illustrated in FIGS. 3-4, the first lumen 30, second lumen 40 and coaxial space 70 of the coaxial catheter device 10 include shapes and diameters of varying sizes. The first lumen 30 comprises a first diameter D1, the second lumen 40 comprises a second diameter D2 and the coaxial space 70 comprises a third diameter D3. The alternating sizes of the diameters of the coaxial catheter device 10 provide for an increase in the performance functionality of each lumen. For example, the third diameter D3 of the coaxial catheter device 10 may be larger than the second diameter D2 and first diameter D1 to enable a physician to easily fill the biliary duct with fluid in a short period of time. In addition, the larger size of the third diameter D3 allows the physician to pass dislodged stones from the biliary duct upon removal. The larger size of the third diameter D3 also provides an increased hydraulic force for removing obstructions of the biliary duct. A skilled artisan would appreciate that other designs utilizing different diameters could also be utilized.

Figure 5:
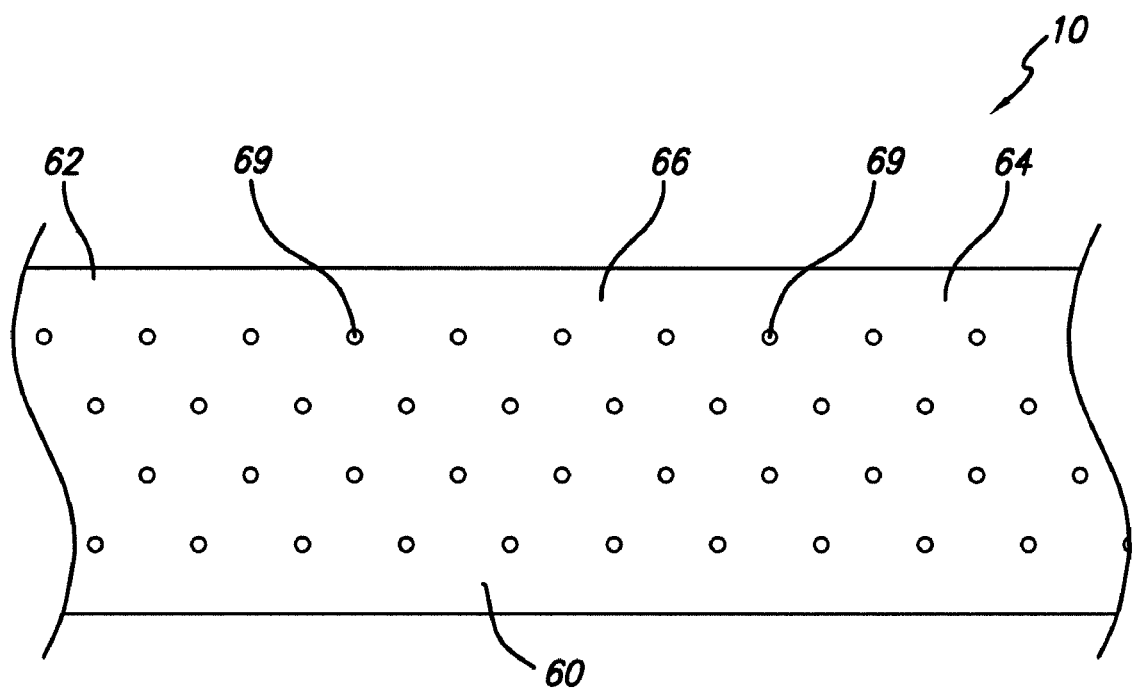
FIG. 5 shows a sectional view of the coaxial catheter device with a coating applied to the surface.

Referring to FIG. 5, an embodiment of the coaxial catheter device 10 is illustrated comprising a coating 69. The coating 69 can be positioned over the entire composite structure or at least portion thereof. Specifically, FIG. 5 shows a partial coating 69 disposed along at least a portion of the surface of the coaxial catheter device 10. Additionally, the coating 69 can be applied to a wire guide or other suitable complimentary medical device used in conjunction with the coaxial catheter device 10. The coating 69 increases the elasticity of the coaxial catheter device 10 when applied to a surface of the device 10. The coating 69 can be hydrophilic or a hybrid polymer mixture, such as those based on polyvinyl pyrolidine in organic solvent solutions. These solutions make the coaxial catheter device 10 particularly lubricious when in contact with body fluids, which aids in navigation. The coating 69 can also include a textured surface, a flat surface or other suitable surface depending on the particular medical procedure.

The coating 69 can be polytetrafluoroethylene, or another suitable material. Examples of suitable coverings include fluoropolymers, polyurethanes, and other suitable coatings used in the medical device arts. The coating 69 may be applied by dipping, molding, or spraying a suitable coating material, such as polytetrafluoroethylene, urethane, and/or other polymeric coatings directly to the desired portions of the coaxial catheter device 10. Alternatively, the coating 69 may be applied by heat shrinking a heat shrinkable material about the desired portions of the coaxial catheter device 10 or other complimentary medical device, such as a wire guide.

One preferred coating comprises a thin PTFE heat shrinkable material. The heat shrinkable nature of these materials facilitates manufacturing while providing a lubricious coating, which facilitates navigation. In preferred embodiments, the thickness of the coating 69 is between approximately 2.5 micrometers and 2.5 millimeters. In some embodiments, the thickness of the coating 69 is between approximately 2.5 micrometers and 100 micrometers. In other embodiments, the thickness of the coating 69 can be between approximately 2.5 micrometers and 50 micrometers. These preferred thicknesses provide suitable coatings while not adding significantly to the overall thickness of the coaxial catheter device 10.

Radiopaque materials known in the art including, but not limited to, bismuth or gold can be added in the coating 69. Also, radiopaque markers known in the art can be placed on the coaxial catheter device 10. Several examples of suitable radiopaque materials and markers are known in the art, and any suitable material and/or marker can be utilized in the present invention.

Figure 6:
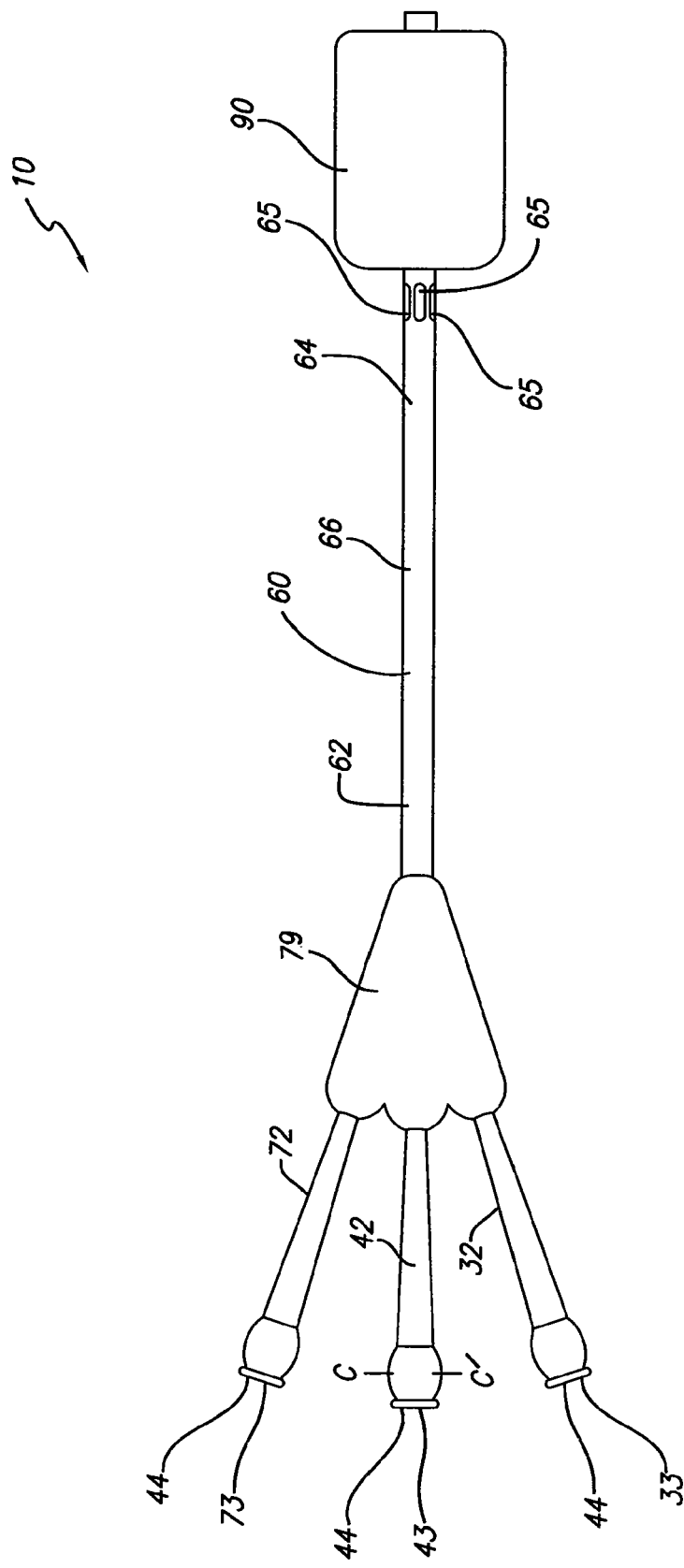
FIG. 6 shows a perspective view of an embodiment of the present invention having an attached connector and balloon.

Referring to FIG. 6, an embodiment of the coaxial catheter device 10 is illustrated that includes a first port 33, second port 43 and a third port 73, wherein each port is associated with an inlet conduit. Specifically, the first port 33 communicates with a first conduit 32 which in turn communicates with the first lumen 30 of the coaxial catheter device 10. The second port 43 communicates with a second conduit 42 which in turn communicates with the second lumen 40 of the coaxial catheter device 10. The third port 73 communicates with a third conduit 72 which in turn communicates with the coaxial space 70 of the coaxial catheter device 10. The combination of each port 33, 43, 73 and corresponding conduit 32, 42, 72 is designed to facilitate the removal and injection of fluid and other items via the passageways created by each lumen 30, 40 and the coaxial space 70 of the coaxial catheter device 10 during medical procedures, such as an ERCP. The conduit 32, 42, 72 of the coaxial catheter device 10 may be comprised of a flexible material to allow for bending and twisting while maneuvering and positioning the coaxial catheter device 10. For example, the conduit 32, 42, 72 may comprise the material polytetraflourethylene (PTFE). However, one skilled in the art would understand that other polymers may be used. In addition, each port 33, 43, 73 may be color coded to identify the function of the corresponding port 33, 43, 73. For example, one color configuration can include a first port 33 identified with a red color, a second port 43 identified with a white color and a third port 73 identified with a blue color. One skilled in the art would understand and appreciate that the color coding of each port 33, 43, 73 is not limited to a specific color combination and may include other suitable configurations.

As illustrated in FIG. 6, the elongated coaxial catheter device 10 can include a connector 79 providing at least three openings to engage each individual port 33, 43, 73 and the corresponding conduit 32, 42, 72 with the corresponding lumen 30, 40, 70. The connector 79 communicates with each inlet port and each lumen of the coaxial catheter device 10.

Figure 7:
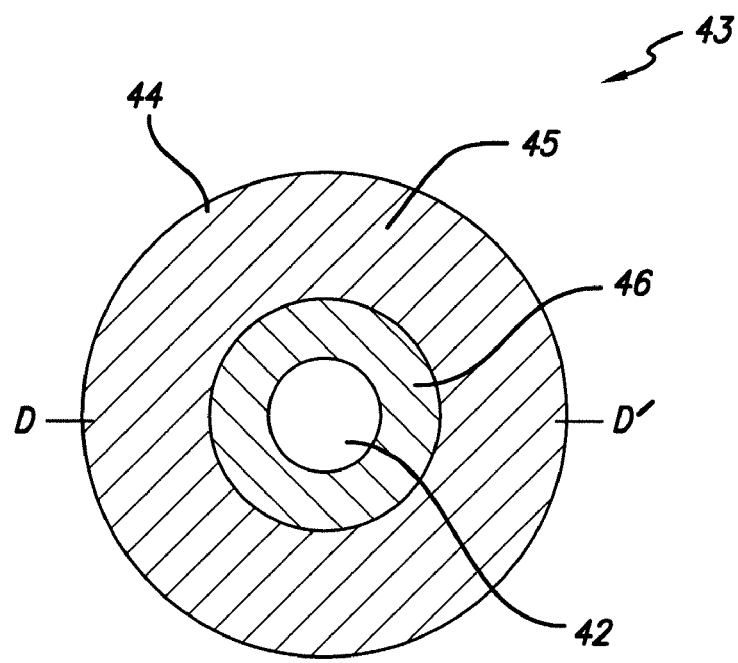
FIG. 7 shows a cross-sectional view of taken along lines C-C' in FIG. 6.
Figure 8:
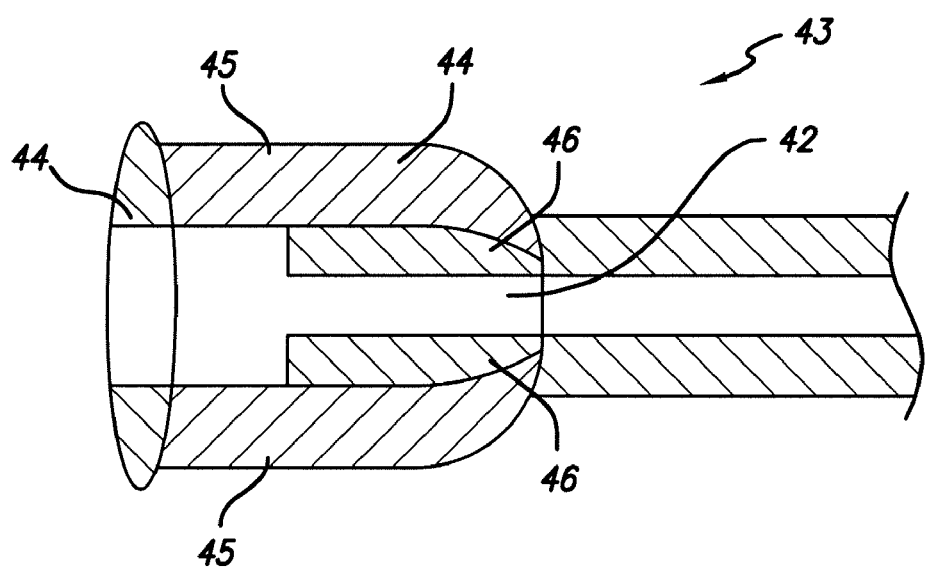
FIG. 8 shows a cross-sectional view taken along lines D-D' in FIG. 7.

In the preferred embodiment, each of the first port 33, second port 43, and third port 73 can comprise a supporting seal 44. Specifically, FIGS. 7-8 illustrate the supporting seal 44 disposed within the second port 43 of the coaxial catheter device 10. The supporting seal 44 can be a multi-part or composite seal comprising a proximal seal 45 and a distal seal 46. The proximal seal 45 and distal seal 46 are each configured to allow probes, needles, or similar elongate devices extending through a lumen of the port to pass through while maintaining an adequate seal there about. For instance, a wire guide can be successfully passed through the second port 43 and the second conduit 42 into the second lumen 40 of the coaxial catheter device 10. Additionally, the supporting seal 44 of the third port 73 can be used to limit the escape of fluids that may be present within the coaxial space 70 of the coaxial catheter device 10 without inhibiting the insertion or movement of the coaxial catheter device 10. This configuration can be of particular benefit in preventing bodily fluids such as bile and blood from escaping and contaminating the physician and the working environment.

The design and configuration of the supporting seal 44, including the types of material from which they are manufactured, are well known to those skilled in the art. An exemplary supporting seal 44 can include slits, torn holes, arranged slits, or penetrable seals may alternatively be used. For example, other seal configurations include duckbill, membrane with a slit (e.g., polystyrene, silicone, or another compliant polymer material), foam seal with small central aperture (e.g., silicon, polyurethane, etc.), or other designs having the ability to secure the coaxial catheter device 10 and prevent any proximally migrating fluid from exiting the third port 73.

In the embodiment illustrated in FIG. 6, the coaxial catheter device 10 further includes a balloon 90 engaged to a distal end of the coaxial catheter device 10. The balloon 90 is utilized to remove biliary stones from the biliary duct of the patient. The balloon 90 is inflated inside the biliary duct above the location of any stones. The biliary duct is then rapidly filled with a fluid, such as water, contrast and saline, utilizing the side port 50. After biliary duct is filled, then the balloon 90 can sweep the biliary duct creating a hydraulic force to remove the stones from the biliary duct. The coaxial space 70 includes the large opening 68 to facilitate an increase in the hydraulic force in the device 10. In a preferred embodiment, the coaxial space 70 is the largest of the triple lumen design providing a lumen size of 0.039". Additionally, in another preferred embodiment, the second lumen 40 is smaller than the coaxial space 70 providing a lumen size of 0.025". The second lumen 40 of the coaxial catheter device 10 is preferably utilized to insert a suitable wire guide. One skilled in the art would understand and appreciate that the lumen size of the coaxial catheter device 10 is not limited to a specific size and may include other suitable sizes depending on the particular catheter configuration.

The coaxial catheter device 10 can also include an exit port 65. The exit port 65 can be utilized as an outlet for flushing fluid infused through a lumen of the coaxial catheter device 10. The device 10 can comprise a plurality of exit ports 65 positioned along the device 10. The exit port 65 can include a diameter of sufficient size to allow fluid to exit the opening of the coaxial catheter device 10 and properly flush a bodily lumen of the patient. As shown in FIG. 6, the exit port 65 of the coaxial catheter device 10 is sized and configured to align along a distal portion of the device 10.

The coaxial catheter device 10 may be preferably formed of molded plastic material. Alternatively, the coaxial catheter device 10 and other component parts, such as the connector, ports, inner catheter and outer catheter, may be formed of any other material as desired by an individual. It should be noted that the component parts of the coaxial catheter device 10 may be formed of a material which may be repeatedly sterilized by medical providers for re-use during medical procedures. Additionally, the coaxial catheter device 10 may be initially sterilized for disposal following use as desired by an individual.

In the preferred embodiment, the coaxial catheter device 10 allows a physician to quickly insert a wire guide into the first lumen 30 of the coaxial catheter device 10 and also insert an inflation fluid into the second lumen 40 of the coaxial catheter device 10. Upon insertion of the wire guide and inflation fluid, the coaxial space 70 and side port 50 are utilized to pass fluid into the biliary duct. The relatively large diameter D3 of the coaxial space 70 allows a greater hydraulic force to be generated. Thus, the physician can properly flush the biliary duct and remove any stones or foreign objects.

In the preferred embodiment of the present invention, at least the first lumen 30 is configured to properly receive and secure the wire guide upon insertion, thereby allowing the wire guide to extend therethrough. Upon insertion, the wire guide can be controlled as it extends through the coaxial catheter device 10 and maneuvered in the patient's body cavity. The diameter of the wire guide can be significantly less than the diameter of the inner lumen of the tubular body. Despite the small diameter, the wire guide is well suited for injecting therapeutics or contrast agents or other treatments prescribed by a physician. The wire guide has sufficient torsional stability to facilitate steering of the wire guide within the lumen of the catheter.

Figure 9:
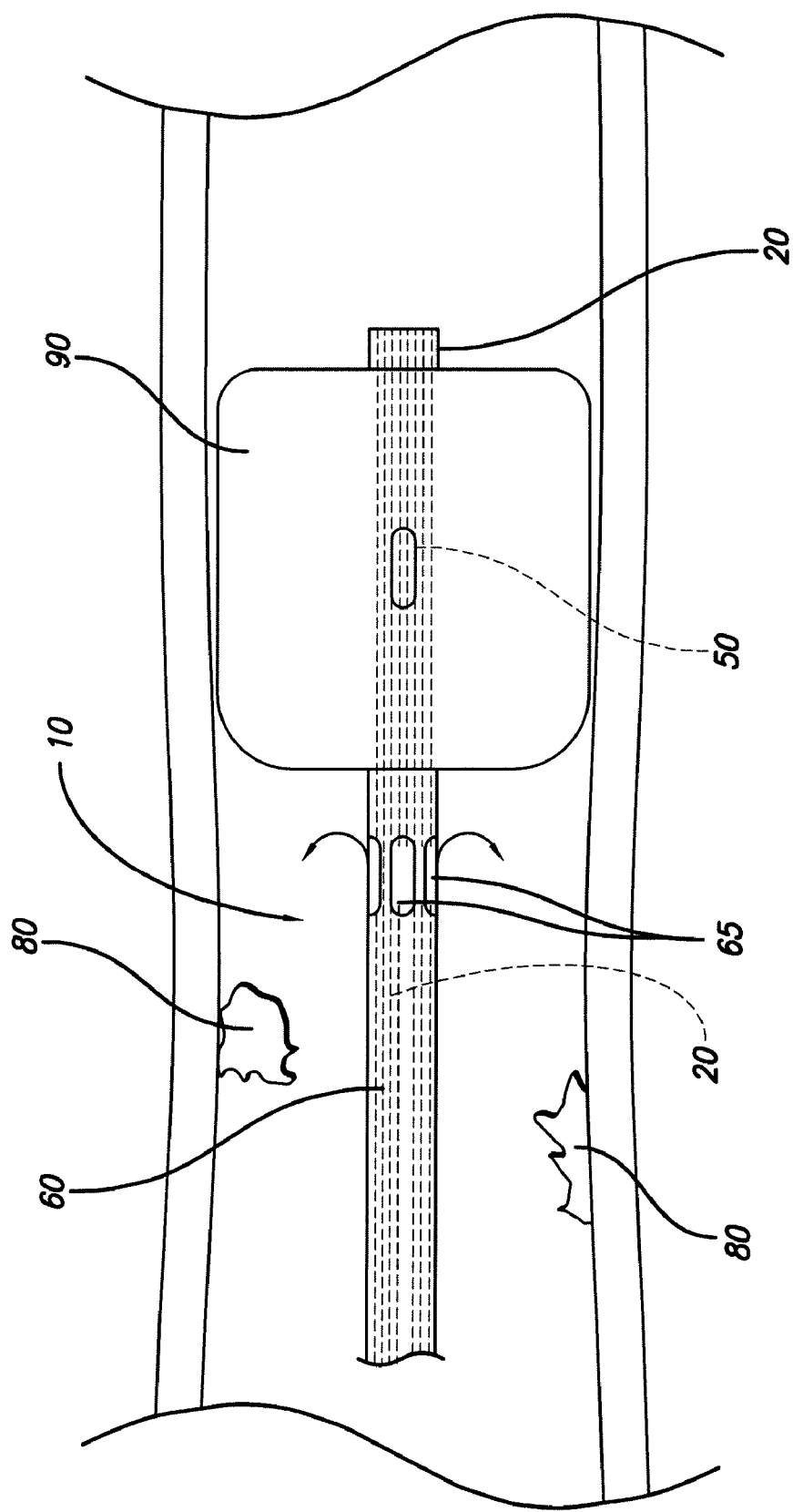
FIG. 9 shows the coaxial catheter device of the present invention positioned in the bodily lumen of a patient.

During use of the coaxial catheter device 10 to remove obstructions of the biliary duct, the device 10 is advanced utilizing a wire guide, as described above, until the desired position is reached. A tracer dye and fluoroscopy may be utilized to assist in the guidance of the coaxial catheter device 10 to the desired location. The coaxial catheter device 10 is passed through the mouth and stomach and into the duodenum until it reaches the point where the common bile duct enters the duodenum. The distal end of the catheter device 10 is then passed into the biliary duct. If an obstruction 80 is encountered, then the balloon 90 is positioned above (upstream) the obstruction 80 as shown in FIG. 9. Subsequently, balloon 90 is inflated to engage the interior surface of the biliary duct. The coaxial catheter device 10 is then flushed by pushing or infusing a fluid through the coaxial space 60 or other opening of the catheter device 10 and out through port 65. This fills the portion of the body lumen below (downstream) the balloon 90 with fluid. The flushing of fluid within this portion of the biliary duct clears any obstruction 80 or object from the biliary duct by urging the obstruction 80 towards the Sphincter of Oddi and into the patient's duodenum.

Novel features of the disclosed catheter device can be successfully used in a variety of applications. Indeed, the coaxial catheter device disclosed herein can be used in a vast number of widely differing medical procedures. In particular, the disclosed catheter device can be used in medical procedures in which one or more elongate medical instruments such as a wire guide or similar device needs to be inserted through a lumen of a patient. Exemplary procedures of this sort are further disclosed and discussed in Application Ser. No. 60/491,408, filed Jul. 31, 2003, Application Ser. No. 60/563,968, filed Apr. 21, 2004, Application Ser. No. 60/565,030, filed Apr. 23, 2004, and Application Ser. No. 60/571,142, filed May 14, 2004, each of which is incorporated herein by reference. Alternatively, the coaxial catheter device 10 can be utilized in conjunction with other medical devices, such as an endoscope to access a biliary duct. The coaxial catheter device 10 is sized and configured so that it can be easily inserted through the accessory port of an endoscope during medical procedures. Catheter devices formed in accordance with the invention can be provided with outer diameters of 3.8, 2.8 and 1.8 mm which allow for use with standard endoscopes having channels with internal diameters of 4.2, 3.2 and 2.2 mm, respectively. In a preferred embodiment, the range of the diameter of the coaxial space is between about 20-70 percent of the diameter of the coaxial catheter device. The use of the coaxial space having a larger diameter facilitates removal of obstructions within the biliary duct while allowing passage of the coaxial catheter device 10 into more remote portions of the biliary tract.

The above figures and disclosures are intended to be illustrative and not exhaustive. This description will suggest many variations and alternatives to one of ordinary skill in the art. All such variations and alternatives are intended to be encompassed within the scope of the attached claims. Those familiar with the art may recognized other equivalents to the specific embodiments described herein which equivalents are also intended to encompass by the attached claims. Moreover, the use of this invention on a wire guide is not a limitation of the claims. Use of this device with other tubing and elongate medical devices used in medical procedures and the like is understood to be within the scope of the claims.

The invention claimed is:

1. A method of removing an obstruction in the biliary duct, comprising the steps of:
   providing a coaxial catheter device comprising an inner catheter having a proximal end and a distal end wherein at least two or more lumens are formed between the proximal end and distal end of the inner catheter;
   providing an outer catheter having a proximal end and a distal end and an opening wherein the inner catheter is coaxially engaged through the opening of the outer catheter thereby forming a coaxial space between the inner catheter and the outer catheter;

inserting a wire guide through a natural opening into the duct and delivering a distal end of the coaxial catheter device through the natural opening distal to the natural opening and into the duct using at least one of the two or more lumens of the coaxial catheter device;

positioning a balloon of the coaxial catheter device distal to the obstruction within the duct;

infusing a fluid into at least one of the two or more lumens of the coaxial catheter device for inflating the balloon; and infusing a fluid into the coaxial space of the coaxial catheter device and out of an exit port of the outer catheter while the balloon is inflated, the exit port positioned proximal to the balloon, to produce a hydraulic force for the removal of an obstruction within the biliary duct out through the natural opening.

2. The method of claim 1 wherein the inner catheter comprises a side port extending along a portion of the inner catheter.

3. The method of claim 2, wherein the side port is utilized to transport fluid selected from the group consisting of water, contrast and saline.

4. The method of claim 1, wherein the exit port and the coaxial space produce the hydraulic force to remove stones from the biliary duct.

5. The method of claim 1 wherein the balloon is engaged to the distal end of the inner catheter of the coaxial catheter device.

6. The method of claim 1 further comprising the step of providing a connector having a first port engaged to a first conduit, a second port engaged to a second conduit and a third port engaged to a third conduit.

7. The method of claim 1 wherein a first lumen includes a first diameter, a second lumen includes a second diameter and the coaxial space includes a third diameter, and wherein the third diameter is larger than first diameter and the second diameter.

8. The method of claim 1 further comprising a radiopaque marker engaged along a surface of the coaxial catheter device.

9. The method of claim 1 further comprising a coating applied to at least a portion of the coaxial catheter device.

10. A method of removing an obstruction in the biliary duct, comprising the steps of:

providing a coaxial catheter device comprising an inner catheter having a proximal end and a distal end, wherein at least two or more lumens are formed between the proximal end and distal end of the inner catheter and wherein the inner catheter comprises a side port extending from along a portion of the inner catheter;

providing an outer catheter having a proximal end and a distal end and an opening, wherein the inner catheter is coaxially engaged through the opening of the outer catheter thereby forming a coaxial space between the inner catheter and the outer catheter;

inserting a distal portion of the coaxial catheter device into a natural opening of the duct and extending the distal portion distally into the duct distal to the natural opening;

infusing a fluid into at least one of the two or more lumens of the coaxial catheter device for inflating a balloon within the duct; and infusing a fluid into a proximal portion of the coaxial space of the coaxial catheter device toward a distal portion of the device and flowing the fluid out of an exit port on a distal portion of the outer catheter for the removal of an obstruction within the biliary duct out through the natural opening.

11. The method of claim 10, wherein the side port is utilized to transport fluid selected from the group consisting of water, contrast and saline.

12. The method of claim 10, wherein the exit port and the coaxial space produce a hydraulic force to remove stones from the biliary duct.

13. The method of claim 10 wherein the balloon is engaged to the distal end of the inner catheter of the coaxial catheter device.

14. The method of claim 10 further comprising the step of providing a connector having a first port engaged to a first conduit, a second port engaged to a second conduit and a third port engaged to a third conduit.

15. The method of claim 10 wherein a first lumen includes a first diameter, a second lumen includes a second diameter and the coaxial space includes a third diameter, and wherein the third diameter is larger than the first diameter and the second diameter.

16. The method of claim 10 further comprising a radiopaque marker engaged along a surface of the coaxial catheter device.

17. The method of claim 10 further comprising a coating applied to at least a portion of the coaxial catheter device.

18. A method of treating a subject comprising:

inserting a coaxial catheter device through a natural opening to a point of treatment within the duct and distal to the natural opening, the coaxial catheter device comprising an inner catheter providing at least two or more lumens coaxially engaged through an outer catheter forming a coaxial space between the inner catheter and the outer catheter wherein at least one of the two or more lumens is configured to receive a fluid for inflating a balloon, at least one of the first lumen and the second lumen is configured to receive a wire guide, and the coaxial space is configured to receive a fluid for removing obstructions from the treatment point;

inflating the balloon at the treatment point;

flowing a fluid into the coaxial space from a proximal portion to a distal portion and out through an exit port with the balloon inflated, the exit port positioned on a distal portion of the outer catheter and proximal to the balloon;

removing the obstruction using the fluid flow to move the obstruction from the treatment point out through the natural opening; and deflating the balloon.

19. The method of claim 1, comprising flushing the obstruction out of the duct by flowing the fluid out of the exit port and sweeping the duct with the balloon.

20. The method of claim 10, providing the exit port positioned proximal to the balloon on the coaxial catheter device.

* * * * *

UNITED STATES PATENT AND TRADEMARK OFFICE
CERTIFICATE OF CORRECTION

| | | |
|---|---|---|
| PATENT NO. | : 8,029,494 B2 | Page 1 of 1 |
| APPLICATION NO. | : 11/585513 | |
| DATED | : October 4, 2011 | |
| INVENTOR(S) | : Kulwinder S. Dua et al. | |

It is certified that error appears in the above-identified patent and that said Letters Patent is hereby corrected as shown below:

<u>On the Title Page</u>

In the left column, item (75), after "Pushkar S. Mukewar, Boston, MA" replace "(US)" with --(IN)--.

Signed and Sealed this

Seventeenth Day of April, 2012

David J. Kappos
*Director of the United States Patent and Trademark Office*